United States Patent [19]

Yasuda et al.

[11] 4,244,918
[45] Jan. 13, 1981

[54] GAS COMPONENT DETECTION APPARATUS

[75] Inventors: Eturo Yasuda; Susumu Sato; Yoshihiro Segawa; Tadashi Hattori, all of Okazaki; Keiji Aoki, Susono, all of Japan

[73] Assignees: Nippon Soken, Inc., Nishio; Toyota Jidosha Kogyo Kabushiki Kaisha, Toyota, both of Japan

[21] Appl. No.: 899,397

[22] Filed: Apr. 24, 1978

Related U.S. Application Data

[63] Continuation-in-part of Ser. No. 751,956, Dec. 17, 1976, Pat. No. 4,099,922.

[30] Foreign Application Priority Data

Apr. 25, 1977 [JP] Japan .................. 52-47702

[51] Int. Cl.³ ............................................. G01N 27/12
[52] U.S. Cl. ..................................... 422/95; 73/27 R; 204/195 S; 324/71 SN; 422/98
[58] Field of Search ............... 422/94, 95, 96, 97, 422/98; 338/34; 73/23, 27 R; 324/71 SN, 65 R, 65 P; 23/232 E; 204/195 S

[56] References Cited

U.S. PATENT DOCUMENTS

| | | | |
|---|---|---|---|
| 3,092,799 | 6/1963 | Baker | 338/34 |
| 3,479,257 | 11/1969 | Shaver | 422/95 X |
| 3,695,848 | 10/1972 | Taguchi | 324/71 SN X |
| 3,699,803 | 10/1972 | Sumi et al. | 338/34 X |
| 3,732,519 | 5/1973 | Taguchi | 338/34 |
| 3,893,230 | 7/1975 | Stadler et al. | 23/232 E X |
| 3,901,067 | 8/1975 | Broadman, Jr. et al. | 73/23 |
| 4,099,922 | 7/1978 | Yasuda et al. | 422/109 |
| 4,151,503 | 4/1979 | Cermak et al. | 73/27 R X |

FOREIGN PATENT DOCUMENTS 2636178  3/1977  Fed. Rep. of Germany ...... 324/71 SN

*Primary Examiner*—Arnold Turk
*Attorney, Agent, or Firm*—Cushman, Darby & Cushman

[57] ABSTRACT

A gas component detection apparatus comprises a first and a second gas sensing elements each composed of a metal oxide which exhibits variable electric resistances according to gaseous components and temperatures of gases to be detected. A catalyst is carried at least by the first sensing element for promoting oxidation reactions of the gaseous components of the gases. A first pair of electrodes are inserted into those portions of the first sensing element which are subjected to catalytic action of the catalyst. Into the portions of the second sensing element which are not subjected to catalytic action are inserted a second pair of electrodes. The first pair of electrodes sense a variation in electric resistances resulting from the gaseous components and temperatures of the gases, while the second pair of electrodes detect an electric resistance variation related mainly upon the gas temperatures. Consequently, an output signal reflecting substantially only the gaseous components of the gases is produced by offsetting both of the electric resistances separately sensed utilizing a suitable electric circuit.

5 Claims, 11 Drawing Figures

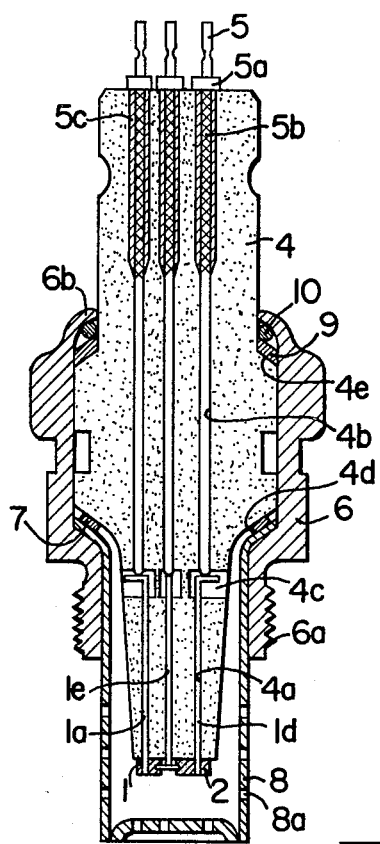

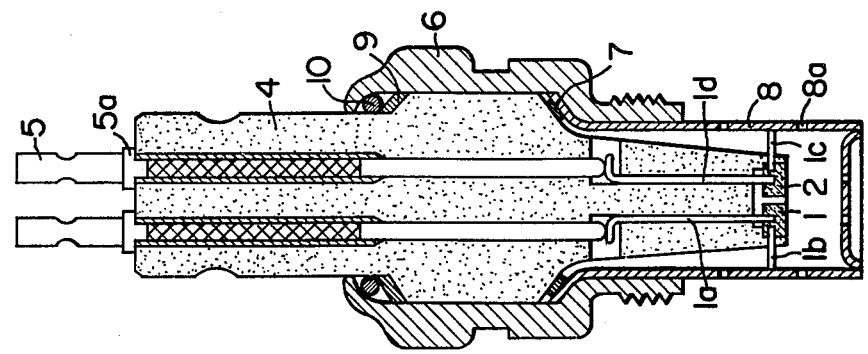

GAS COMPONENT DETECTION APPARATUS

CROSS-REFERENCE TO RELATED APPLICATION

The present application is a continuation-in-part of the applicants' earlier U.S. patent application, Ser. No. 751,956, filed on Dec. 17, 1976, now Pat. No. 4,099,922 dated July 11, 1978.

BACKGROUND OF THE INVENTION

The present invention relates to a gas component detection apparatus for detecting the variation in concentrations of gaseous components such as oxygen ($O_2$), carbon monoxide (CO) and hydrocarbon (HC) of for example exhaust gases from an internal combustion engine.

Gas component detection apparatuses have been widely used in many industrial fields. Lately, as a countermeasure to cope with the problem of exhaust gases from an internal combustion engine, gas component detection apparatus have been employed for determining the air-fuel ratio of an air-fuel mixture supplied to the internal combustion engine.

In the case where a catalyst is utilized for purifying exhaust gases from an internal combustion engine, the catalyst cannot exhibit maximum properties unless the air-fuel ratio of an air-fuel mixture is maintained constantly at a proper value. However, in an ordinary internal combustion engine equipped with a conventional carburetor or a fuel injection apparatus, the air-fuel ratio is actually inevitably subjected to a large variation even when the ratio of an injected fuel to intake air is set to be constant. Consequently, in order to maintain constantly a proper air-fuel ratio, it is necessary to detect with the use of gas detection apparatus the air-fuel ratio prior to burning of the air-fuel mixture and feed back a signal corresponding to the detected value to the carburetor or the injection apparatus, thereby controlling the air-fuel ratio of the air-fuel mixture supplied to the engine.

Gas component detection apparatuses are constructed to determine the air-fuel ratio based on the fact that the variation in concentrations of gaseous components of the exhaust gases is closely related to variation of the air-fuel ratio of the air-fuel mixture. In this connection, consideration has to be given to the fact that the temperature of the exhaust gases, as well as the concentrations of the gaseous components thereof, will vary abruptly and remarkably. It is thus desirable that the gas component detection apparatuses be operable with high accuracy notwithstanding such prominent variables.

Heretofore, a gas component detection apparatus has been known which employs transition metal oxide. In the case where the air-fuel ratio of an air-fuel mixture is determined by employing such detection apparatus, a differential operational amplifier which has a non-inverted input terminal and an inverted input terminal is used. The detection apparatus is mounted for example in an exhaust pipe of an internal combustion engine with the transition metal oxide exposed to the exhaust gases, and the electric resistance variation thereof is detected. A reference voltage set by reference resistors is applied to the non-inverted input terminal of the amplifier, and a voltage established by the electric resistance of the transition metal oxide is applied to the inverted terminal of the amplifier. The amplifier compares the voltages applied to both its input terminals and produces a corresponding output signal, and the latter signal can be utilized to control the air-fuel ratio of the air-fuel mixture supplied to the internal combustion engine.

However, in order to effect proper control of the air-fuel ratio by employing the abovementioned detection apparatus, it is necessary to compensate the electric resistance variation of the transition metal oxide due to temperature variation of the exhaust gases since the electric resistances exhibited by the transition metal oxide vary depending upon not only the concentrations of the gaseous components of the exhaust gases, but also the temperature thereof. For example, in the case where the reference voltage is set to control the air-fuel ratio to the stoichiometrical one at an exhaust gas temperature of 850° C., the control can be preferably effected at this temperature. However, when the exhaust gas is at 350° C., the determined air-fuel ratio is smaller than the stoichiometrical one, which makes precise control of the air-fuel ratio impossible.

SUMMARY OF THE INVENTION

It is therefore an object of the present invention to provide a gas component detection apparatus which can detect with high accuracy gaseous components of exhaust gases or the like, without being influenced by the temperature of the latter.

It is another object of the invention to provide a gas component detection apparatus which can be used for controlling the air-fuel ratio of an air-fuel mixture supplied to combustion devices such as an internal combustion engine.

It is a further object of the invention to provide a gas component detection apparatus which can be easily manufactured.

According to one aspect of the present invention, there is provided a gas component detection apparatus comprising a first and a second gas sensing elements each including a metal oxide which exhibits variable electric resistances according to gaseous components and temperatures of gases to be detected, a catalyst carried by the first sensing element for promoting oxidation reactions of the gaseous components of the gases, a first pair of electrodes inserted into the first sensing element for sensing a variation in electric resistances exhibited at that portion of the first sensing element subjected to catalytic action of the catalyst and resulting from the gaseous components and temperatures of the gases, and a second pair of electrodes inserted into the second sensing element for sensing an electric resistance variation resulting from mainly the gas temperatures.

According to another aspect of the invention, also the second sensing element carries a catalyst for promoting oxidation reactions of gaseous components of the gases to be detected. The second pair of electrodes are inserted into those portions of the second sensing element which are not subjected to catalytic action of the catalyst carried thereon. The catalyst carried by the second sensing element serves to maintain the latter element at substantially same temperature as that of the first sensing element when both first and second sensing elements are exposed to the gases to be detected. Consequently, the detection apparatus can detect concentrations of the gaseous components with further improved accuracy.

The gas component detection apparatus of the invention is preferably used with an internal combustion engine to determine whether the air-fuel ratio of the air-fuel mixture supplied thereto is larger or smaller than the stoichiometrical air-fuel ratio, thereby controlling the air-fuel ratio of the air-fuel mixture supplied into the engine at the stoichiometrical air-fuel ratio.

The above and other objects as well as novel features and advantages of the invention will become more apparent from the following description when read in conjunction with the accompanying drawings.

BRIEF DESCRIPTION OF THE DRAWINGS

FIG. 3 is a vertical sectional view of a first embodiment of a gas component detection apparatus according to the invention;

FIG. 4 is an enlarged sectional view showing a first and second sensing elements used in the detection apparatus shown in FIG. 3;

FIG. 5 is an explanative sectional view showing the first and second sensing elements of FIG. 4, with their electrodes not welded together;

FIG. 6 is a schematic diagram of one example of an electric circuit for determining and controlling the air-fuel ratio utilizing the detection apparatus according to the invention;

FIG. 7 is a schematic diagram similar to FIG. 6 showing another example of an electric circuit;

FIGS. 8A to 8C are sectional views similar to FIG. 1, showing essential parts of the gas component detection apparatus according to a second embodiment of the invention; and FIG. 9 is a vertical sectional view similar to FIG. 3, showing a third embodiment of a gas component detection apparatus according to the invention.

Same or similar reference numerals are used to designate same or similar parts throughout the figures.

DESCRIPTION OF THE PREFERRED EMBODIMENTS

Figure 1:
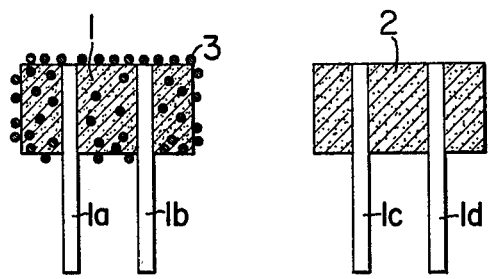
FIG. 1 is a sectional view of a first and a second gas sensing elements, explaining a principle of a gas component detection apparatus according to the present invention.

First of all, the underlying principle of the present invention will be described with reference to FIGS. 1 and 2. Referring first to FIG. 1, a first gas sensing element 1 is composed of a plate-like sintered mass of titanium oxide, and carries a catalyst 3 composed of platinum or the like not only on its surfaces but also within the element 1. Into the portions of the element 1 subjected to catalytic action of the catalyst 3 are inserted a pair of electrodes 1a and 1b. A second gas sensing element 2 is composed of a plate-like sintered mass of titanium oxide as is similar to the first sensing element 1, and a pair of electrodes 1c and 1d are inserted thereinto. The second element 2 carries thereon no catalyst.

Upon usage, the first and second sensing elements 1 and 2 are exposed for example to the exhaust gases emitted from an internal combustion engine. As is well-known, the exhuast gases contain gaseous components such as oxygen ($O_2$), nitrogen oxides ($NO_x$), carbon monoxide (CO), hydrocarbon (HC) and hydrogen ($H_2$), and the concentration of each of these gaseous components varies depending upon the air-fuel ratio of an air-fuel mixture prior to burning. In general, sensing elements of this type exhibit variable electric resistances according to the variation in the overall exhaust gas condition brought about by variations in the partial pressures of these individual gaseous components. Further, this type of the sensing elements are influenced by the temperature of the exhaust gases, and exhibit variable electric resistances according to this temperature.

When the first sensing element 1 is exposed to the exhaust gases, for example the following reactions will take place because of the presence of the catalyst 3.

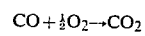

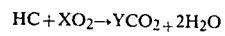

(In these formulae, X and Y indicate suitable coefficients.) As a result, the $O_2$ partial pressure of the exhaust gases changes greatly on the surfaces of the first sensing element 1 when the surrounding atmosphere changes from the reduction to the oxidation atmosphere and vice versa, and this variation in $O_2$ partial pressure may be identified in terms of the variation in electric resistances sensed between the pair of electrodes 1a and 1b. This variation in electric resistances is remarkable in the vicinity of the stoichiometrical air-fuel ratio.

On the other hand, the variation in the $O_2$ partial pressure caused on the surfaces of the second sensing element 2 is not so remarkable as that of the first sensing element 1 because the second sensing element 2 carries no catalyst. Thus, the variation in electric resistances sensed between the electrodes 1c and 1d of the second sensing element 2 mainly reflects the variation in temperature of the exhaust gases.

As will be understood from the foregoing, the electrodes 1a and 1b of the first sensing element 1 detect the electric resistance variation which depends upon both the gaseous components and the exhaust gas temperature, while the electrodes 1c and 1d of the second sensing element 2 senses the electric resistance variation resulting mainly from the exhaust gas temperature. It should be noted that the value of the electric resistance variation present at the electrodes 1a and 1b depending on the exhaust gas temperature variation is substantially identical with the value of the electric resistance variation which is sensed between the electrodes 1c and 1d of the second element 2 which also has resulted from the exhaust gas temperature variation, since both elements 1 and 2 are composed of the same metal oxide.

Figure 2:
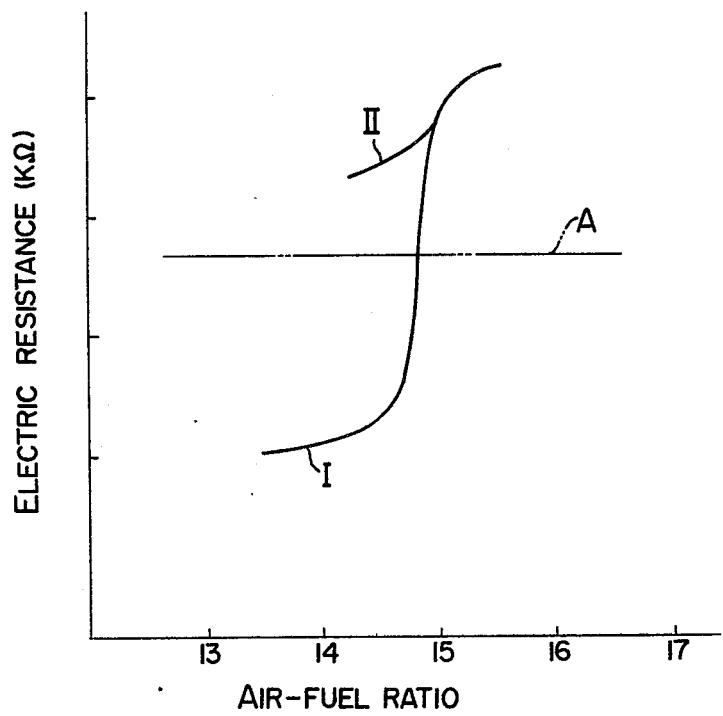
FIG. 2 graphically shows the relationship between the air-fuel ratio of an air-fuel mixture and the electric resistances sensed at pairs of electrodes incorporated in the first and second sensing elements, respectively.

FIG. 2 graphically shows a relationship between the air-fuel ratio of the air-fuel mixture and the electric resistances sensed at the respective pairs of electrodes. In FIG. 2, curve I shows the relationship between the air-fuel ratio and electric resistance variations resulting from both the exhaust gas temperature and the gaseous components, which were sensed between the electrodes 1a and 1b of the first sensing element 1, while curve II shows the relationship between the air-fuel ratio and electric resistance variations dependent mainly upon the exhaust gas temperature, which were sensed between the electrodes 1c and 1d of the second sensing element 2. These curves I and II were obtained by an experiment in which the sensing elements 1 and 2 and the catalyst 3 were composed of titanium oxide ($TiO_2$) and platinum (Pt), respectively. Additionally, the exhaust gas was at a temperature of 600° C. In the FIG. 2 graph, the ordinate indicates electric resistance (KΩ) in a logarithm scale, while the abscissa indicates the air-fuel ratio of the air-fuel mixture with an equally divided scale. As described, the value of the electric resistance variation detected at the electrodes 1a and 1b and dependent on the exhaust gas temperature variation is substantially identical with the value of the electric resistance variation dependent on exhaust gas temperature variation sensed between the electrodes 1c and 1d. Therefore, characteristic curves similar to the curves I and II of FIG. 2 can be obtained at different exhaust gas temperatures. This means that the variation in electric resistance sensed between the pair of electrodes 1a and 1b of the first sensing element 1 may be compensated by the variation in electric resistance detected at the pair of electrodes 1c and 1d of the second sensing element 2, so as to determine an exact stoichiometrical air-fuel ratio regardless of the variation in temperature of the exhaust gases.

FIGS. 3 to 5 show a first embodiment of the invention. The first embodiment includes a first and second gas sensing elements 1 and 2 each composed of a plate-like sintered mass of titanium oxide. When preparing the sensing elements 1 and 2, a powder of titanium oxide (in a rutile structure) sintered at a temperature of about 1200° C. is finely divided into particles having average diameters of 0.1 to 3 microns utilizing a ball mill or the like. The finely divided power is then kneaded in a kneader with an organic binder solution into a slurry. Thereafter, the slurry is formed by a doctor blade process into sheets each having a thickness of about 0.2 mm, and a few of the sheets are overlayed into two layers of appropriate thickness with pairs of platinum electrodes 1a, 1b and 1c, 1d inserted into the respective sheet layers. The sheet layers having the electrodes inserted thereinto are then pressed and sintered to form the sensing elements 1 and 2. Catalysts 3 are carried on and within the first sensing element 1, as further described hereunder. The electrodes 1b and 1c of the first and second sensing elements and an additional platinum electrode 1e are welded together so that the sensing elements 1 and 2 may be electrically connected in series. The catalysts 3 composed of platinum are carried on and within the first sensing element 1, for example by impregnating the sensing element 1 in chloroplatinate ($H_2PtCl_4.6H_2O$), in turn deoxidizing the same in a hydrogen current and in turn sintering the same. Alternatively, an evaporation process may be used for this purpose. In either case, care should be taken so that the electrical short-circuit between the electrodes 1a and 1b may be avoided. The outer end faces of the electrodes 1a and 1d are exposed to the outer surfaces of the sensing elements 1 and 2, respectively.

The first and second sensing elements 1 and 2 thus prepared are fixed to the lower end of a refractory, electrically insulative protecting body 4 made of for example alumina, and the electrodes 1a, 1e and 1d are inserted into vertical electrode holes 4a formed in the lower portion of the protecting body 4. Metal lead wires 5 each having a flange 5a and a knurled portion 5b are inserted into vertical lead wire holes 4b formed in the upper portion of the protecting body 4, and the knurled portions 5b of the lead wires 5 are securely jointed to the protecting body 4 with a glass ceramic adhesive 5c or the like. The lower ends of the lead wires 5 and the upper ends of the electrodes 1a, 1e and 1d are electrically contacted with each other in lateral holes 4c in the protecting body 4 and are securely jointed to each other by the laser spot welding.

The protecting body 4 with the first and second sensing elements 1 and 2 incorporated therein is inserted into a housing 6 which is made of a refractory metal and has externally threaded screws 6a for mounting the gas detection apparatus on for example an exhaust pipe (not shown) of an automotive vehicle. A washer 7 made of a refractory metal and the upper portion of a protecting cover 8 made of a refractory metal are securely clamped between the lower tapered portion 4d of the protecting body 4 and the mating tapered inner surface of the housing 6. The protecting cover 8 is formed with small holes 8a for permitting the flow of exhaust gases into and out of the protecting cover 8. Between the upper end 6b of the housing 6 and the shoulder portion 4e of the protecting body 4 are interposed a washer 10 and a ring 9 made of a relatively soft metal such as copper. The upper end 6b of the housing 6 is radially inwardly bent toward the protecting body 4 to securely joint together the housing 6 and the protecting body 4.

FIG. 6 shows one example of an electric circuit incorporating the gas component detection apparatus of the invention. In this circuit, the second sensing element 2 not carrying the catalysts is represented by a detector resistor $R_3$ between the electrodes 1d and 1c, while the first sensing element 1 carrying the catalysts 3 is represented by another detector resistor $R_4$ between the electrodes 1a and 1b. The detector resistors $R_3$ and $R_4$ are connected in series, and an intermediate point x is connected to an inverted input terminal (−) of a differential operational amplifier C via electrode 1e. Reference resistors $R_1$ and $R_2$ are connected in series, and a reference voltage established by these reference resistors is adapted to be applied to the non-inverted other input terminal (+) of the amplifier C. At the intermediate point x, the electric resistance variation sensed across the electrodes 1a and 1b due to the temperature variation of the exhaust gases is substantially offset or cancelled by the electric resistance variation across the electrodes 1d and 1c due to this exhaust gas temperature variation. Consequently, there is established at the intermediate point x a voltage representing only the abrupt electric resistance variation produced by the gaseous components. In other words, the voltage obtained at the intermediate point x substantially depends upon the concentrations of the gaseous components or the air-fuel ratio.

The electric resistance value of the first sensing element 1 will exhibit an abrupt variation when the actual or detected air-fuel ratio is changed from the stoichiometrical air-fuel ratio. Thus, in order to control the actual air-fuel ratio to the stoichiometrical air-fuel ratio, the reference voltage established by the reference resistors to represent the stoichiometrical air-fuel ratio (such reference voltage being indicated by a phantom line A in FIG. 2 in terms of electric resistance) is applied to the non-inverted input terminal (+) of the amplifier C. The amplifier C compares the voltage applied to both its input terminals, and issues a corresponding output signal for operating an actuator D comprising for example, an air-fuel ratio compensation unit of a carburetor. In the case where the detected air-fuel ratio is larger than the stoichiometrical air-fuel ratio whereby the voltage at the intermediate point x is larger than the reference voltage representing the stoichiometrical air-fuel ratio, the amplifier C issues an output signal for operating the actuator D to make the air-fuel ratio smaller, thereby reducing it to the stoichiometrical one. On the other hand, in the case where the detected air-fuel ratio is smaller than the stoichiometrical one and the voltage at the intermediate point x is smaller than the reference voltage, the output signal issued from the amplifier C operates the actuator D to make the air-fuel ratio larger so as to increase it to the stoichiometrical one. In FIG. 6, a character V designates an electric source such as battery.

As will be understood from the foregoing, with the structure of the detection apparatus according to the invention, the electric resistance variation exhibited at the first sensing element 1 carrying the catalysts 3 and that exhibited at the second sensing element 2 not carrying the catalysts can be detected separately. Thus, it becomes possible to offset the electric resistance variation exhibited at the first element 1, due to the exhaust gas temperature variation, by the electric resistance variation exhibited at the second element 2. Consequently, the precise determination of the actual air-fuel ratio can be constantly made.

It will be understood that the electric circuit shown in FIG. 6 is only one example of a circuit which may be employed. Another electric circuit, such as that shown in FIG. 7, also may be used. In the circuit of FIG. 7, the reference resistor $R_2$ and the detector resistor $R_4$ are connected in series, while the reference resistor $R_1$ and the detector resistor $R_3$ also are connected in series. The voltage established at the intermediate point x' between the reference resistor $R_2$ and the detector resistor $R_4$ is applied via electrode 1e to the inverted input terminal (−) of the amplifier C, while the voltage established between the reference resistor $R_1$ and the detector resistor $R_3$ is applied to the non-inverted input terminal (+) of the amplifier C. The remaining structure of this circuit is substantially similar to the electric circuit of FIG. 6. Accordingly, the same or similar parts are indicated by the corresponding reference numerals and characters in these figures. With the circuit of FIG. 7, the electric resistance variation sensed between the electrodes 1a and 1c due to the temperature variation of the exhaust gases is substantially offset by the electric resistance variation between the electrodes 1a and 1b due to this temperature variation.

FIGs. 8A to 8C illustrate essential parts of a second embodiment of the gas component detection apparatus in accordance with the invention. In this second embodiment, the second sensing element 2 carries catalyst 3a as does the first sensing element. The catalysts 3a are composed of platinum or the like. Electrodes 1c and 1d are so positioned that the electric resistances sensed thereacross may not be affected by the catalytic action of the catalysts 3a, since the primary function of the second sensing element 2 is to detect the variation in electric resistances due to the variation in the exhaust gas temperature. In the first embodiment described, a reaction heat resulting from catalytic action of the catalyst carried on and within the first sensing element causes a temperature rise at the surface of the latter. Since the second sensing element 2 in the second embodiment carries the catalysts 3a, the temperature rise occurs also at the surface of the second sensing element 2 due to the catalytic action of the catalysts 3a so that the temperature difference between the first and second sensing elements 1 and 2 may be substantially eliminated. Consequently, the accuracy in detection performance of the detection apparatus may be improved.

FIG. 9 shows a third embodiment of the invention. In this embodiment, one of the electrodes 1b of the first sensing element 1 and one of the electrodes 1c of the second sensing element 2 are welded to the protecting cover 8 so that they may be grounded. The third embodiment does not comprise an electrode corresponding to the electrode 1e of the first embodiment, so that the first and second sensing elements are not electrically connected. It will be apparant that the detection apparatus of this third embodiment can detect the concentrations of gaseous components by utilizing a suitable electric circuit. The remaining structure of the third embodiment is substantially similar to the first embodiment described hereinbefore. It will be understood that the second sensing element 2 of this third embodiment may carry the catalysts in the same manner as the second sensing element of the second embodiment shown in FIGS. 8A to 8C.

Although the first and second sensing elements 1 and 2 of the above-described embodiments are composed of titanium oxides ($TiO_2$), these sensing elements may be composed of tin oxide ($SnO_2$). Alternatively, each of these sensing elements may be composed of a plurality of different metal oxides such as zirconium oxide ($ZrO_2$), nickel oxide (NiO), cerium oxide ($CeO_2$) and zinc oxide (ZnO). The latter metal oxides exhibit substantially same resistance variation for the same temperature variation.

It is preferable that the first sensing element 1 has a porous structure so that the gases to be detected may easily penetrate into this element. With this structure, the first sensing element becomes very sensitive to the variation in concentrations (partial pressures) of gaseous components of the gases. Also it is preferable that the second sensing element 2 has a dense structure so as to prevent the gases from penetrating into this element. This structure makes the second sensing element substantially free from the influence of the gaseous components.

In order to make the second sensing element substantially free from the influence of the gaseous components, it is also effective to add chromium oxide ($Cr_2O_3$) or manganese oxide ($MnO_2$) to the second sensing element. For example, more than 5 atm % of chromium oxide or more than 1 atm % of maganese oxide may be added to the second sensing element composed of titanium oxide. In the case where chromium oxide or manganese oxide is added to the second sensing element having the dense structure as described above, the properties in this respect of the latter element is further improved.

The first sensing element may be constituted by a thin film carried on a base body which is composed of a refractory, electrically insulative metal oxide. In this case, the sensing element is carried thereon as the thin film having a thickness of about 100 angstroms to 100 microns, by means of for example vacuum evaporation or spattering process. The catalysts are carried on and/or within the thin film for example by electric beam evaporation. The platinum electrodes may be formed by a paste firing process or an evaporation process. Similarly, the second sensing element may be constituted by the abovementioned thin film carried on the base body.

In order to prevent that impurities such as phosphor, lead and the like in the gases to be detected are attached to the surfaces of the first and second sensing elements directly exposed to the gases, the latter surfaces may be covered with electrically insulative and gas permeable porous ceramic films which are composed of for example γ-almina.

The gas component detection apparatus according to the present invention comprises two gas sensing elements which function separately in cooperation with the corresponding electrodes. This structure makes the manufacture of the sensing elements easier as compared with the structure in which a single sensing element partially carrying the catalyst is used. Additionally, the structure of the invention in which temperature compensation is effected with the second sensing element improves accuracy in temperature compensation, as compared with the case where the temperature compensation is effected utilizing a thermocouple, a thermistor or the like. The latter structure is advantageous also from the standpoint of prices of the detection apparatus.

What is claimed is:

1. A gas component detection apparatus comprising:
   first and second gas sensing elements each including a metal oxide which exhibits variable electric resistances according to gaseous components and temperatures of gases to be detected;
   a catalyst carried by said first sensing element for promoting oxidation reactions of the gaseous components of the gases,
   a first pair of electrodes inserted into said sensing element for sensing a variation in electric resistance exhibited at that portion of said first sensing element subjected to catalytic action of said catalyst and resulting from the gaseous components and temperatures of the gases,
   a second pair of electrodes inserted into said second sensing element for sensing an electric resistance variation resulting mainly from the gas temperature,
   circuit means adapted to be joined to said sensing elements for producing an output signal, and
   means connecting the electrodes of the sensing elements to the circuit means in a manner whereby the variations in resistance of the sensing elements resulting from the gas temperatures offset one another and said output is representative of variations in resistance of the first sensing element resulting from the gaseous components.

2. A gas component detection apparatus as set forth in claim 1, wherein the metal oxide of each of said first and second sensing elements includes a plurality of different metal oxides, said oxides exhibiting substantially the same resistance variation for the same temperature variation.

3. A gas component detection apparatus as set forth in claim 1 or 2, wherein said first sensing element has a porous structure, while said second sensing element has a dense structure.

4. A gas component detection apparatus as set forth in claim 3, wherein said second sensing element includes chromium oxide as an additional oxide.

5. A gas component detection apparatus as set forth in claim 3, wherein said second sensing element includes manganese oxide as an additional oxide.

* * * * *

UNITED STATES PATENT AND TRADEMARK OFFICE
CERTIFICATE OF CORRECTION

PATENT NO. : 4,244,918
DATED : January 13, 1981
INVENTOR(S) : Eturo Yasuda et al.

It is certified that error appears in the above—identified patent and that said Letters Patent is hereby corrected as shown below:

On the title page, Foreign Application Priority Data should read:

-- Dec. 23, 1975 (JP)    Japan        50-154334
   Apr. 25, 1977 (JP)    Japan        52-47702 --

Signed and Sealed this

Second Day of March 1982

[SEAL]

Attest:

Attesting Officer

GERALD J. MOSSINGHOFF
Commissioner of Patents and Trademarks